United States Patent
Harris et al.

(10) Patent No.: US 10,024,810 B2
(45) Date of Patent: *Jul. 17, 2018

(54) ON-BELT ANALYSER SYSTEM

(71) Applicant: SCANTECH INTERNATIONAL PTY LTD, Camden Park, South Australia (AU)

(72) Inventors: Andrew Roland Harris, Seaview Downs (AU); Michael Francis Edwards, Glenunga (AU); Kenneth Graham Smith, Wayville (AU); Gavin Leith Christie, Golden Grove (AU); Nick John Deans, Woodcroft (AU)

(73) Assignee: SCANTECH INTERNATIONAL PTY LTD, Camden Park (AU)

( * ) Notice: Subject to any disclaimer, the term of this patent is extended or adjusted under 35 U.S.C. 154(b) by 198 days.

This patent is subject to a terminal disclaimer.

(21) Appl. No.: 13/837,700

(22) Filed: Mar. 15, 2013

(65) Prior Publication Data

US 2013/0193328 A1   Aug. 1, 2013

Related U.S. Application Data

(63) Continuation of application No. 11/817,657, filed as application No. PCT/AU2006/000263 on Mar. 1, 2006, now Pat. No. 8,426,821.

(Continued)

(30) Foreign Application Priority Data

Mar. 1, 2005   (AU) ................................ 2005900951

(51) Int. Cl.
   *G01N 23/222*   (2006.01)
   *G01N 23/22*   (2018.01)

(52) U.S. Cl.
   CPC .......... *G01N 23/222* (2013.01); *G01N 23/22* (2013.01); *G01N 2223/309* (2013.01); *G01N 2223/617* (2013.01); *G01N 2223/643* (2013.01)

(58) Field of Classification Search
   CPC ...... G01N 23/16; G01N 23/222; G01N 23/22; G01N 2223/309; G01N 2223/617; G01N 2223/643

(Continued)

(56) References Cited

U.S. PATENT DOCUMENTS 3,278,747 A * 10/1966 Ohmart .................. G01G 9/005
                                                    177/16
3,761,712 A *  9/1973 Listerman ..................... 250/388

(Continued)

FOREIGN PATENT DOCUMENTS

DE   44 14 434   11/1995
EP   0 096 092   12/1983

(Continued)

OTHER PUBLICATIONS

Lindstrom, Richard M., "Prompt-Gamma Activation Analysis," Journal of Research of the National Institute of Standards and Technology, vol. 98, No. 1, Jan.-Feb. 1993, pp. 127-133.*

(Continued)

*Primary Examiner* — David Porta
*Assistant Examiner* — Carolyn Igyarto
(74) *Attorney, Agent, or Firm* — Hamre, Schumann, Mueller & Larson, P.C.

(57) ABSTRACT

An analyzer system including an on-belt analyzer having a housing adapted to be positioned across a path of a conveyor belt which carries material to be analyzed, wherein the housing defines a tunnel dimensioned to allow the belt to travel therethrough in suspended relation in order to allow (Continued)

analysis of the material without the belt contacting the analyzer.

19 Claims, 4 Drawing Sheets

Related U.S. Application Data

(60) Provisional application No. 60/658,195, filed on Mar. 2, 2005.

(58) Field of Classification Search
USPC .............................. 250/358.1, 360.1, 455.11
See application file for complete search history.

(56) References Cited

U.S. PATENT DOCUMENTS

| | | | |
|---|---|---|---|
| 5,825,030 | A | 10/1998 | Hurwitz et al. |
| 6,034,629 | A | 3/2000 | Heo et al. |
| 6,362,477 | B1 | 3/2002 | Sowerby et al. |
| 2003/0147484 | A1 | 8/2003 | Olshansky et al. |
| 2003/0225531 | A1* | 12/2003 | Lingren .................... G01T 3/06 702/23 |
| 2004/0245449 | A1 | 12/2004 | Nakashige et al. |
| 2005/0004763 | A1 | 1/2005 | Osucha et al. |

FOREIGN PATENT DOCUMENTS

| | | |
|---|---|---|
| EP | 0 866 332 | 9/1998 |
| WO | 03/056317 | 7/2003 |
| WO | 2004/033117 | 4/2004 |

OTHER PUBLICATIONS

On Belt Analyser Operation & Maintenance Manual Version 1.3, Sep. 2005.
On Belt Analyser-5 Health & Safety Review Version 1.6, Feb. 2006.
On Belt Analyser Installation Manual Version 7.3, Oct. 2005.
SABIA, Inc., XC-5000 OnBelt Elemental Coal Analyzer Site Preparation Manual, Rev A., Nov. 2003, 25 pages.
Foster, "Two Cases Studies—Use of Across-the-Belt Analyzers to meet Train Quality Targets", International On-line coal Analyzer Technical Conference, Nov. 2004, 15 pages.
SABIA, Inc., XL-5000 OnBelt Elemental Cement Analyzer, Site Preparation Manual, Rev A. Nov. 2003, pp. 1-24.
Foster, et al., "Lafarge, Whitehall Opts for PGNA Analyser", Feb. 2009, pp. 67-70, http://sabiainc.org/LafargeWhitehallPGNAAnalyser.pdf.
SABIA's XL5000 OnBelt Cement Analyzer photograph—1 page.
Sabia, Inc. On-Belt Analyzer Radiation Survey Sheet Material Analyzer XC-5000 (Shutter Close) dated Aug. 12, 2003, performed for RAG Twentymile Mine Coal Co.—1 page.
Sabia, Inc. On-Belt Analyzer Radiation Survey Sheet Material Analyzer XC-5000 (Shutter Open) dated Aug. 12, 2003, performed for RAG Twentymile Mine Coal Co.—1 page.
U.S. Nuclear Regulatory Commission—Registry of Radioactive Sealed Sources and Devices Safety Evaluation of Device, and attachment, dated Nov. 2, 2004—18 pages.
SABIA, Inc. Nuclear Source Leak Test report dated Aug. 12, 2003 performed for RAG Twentymile Mine Coal Co.—1 page.
Third party Declarations and exhibits submitted to the Australian Patent Office in corresponding Australian Patent Application No. 2006220232, Jul. 23, 2012—25 pages.
Third party Declaration and exhibits submitted to the Australian Patent Office in corresponding Australian Patent Application No. 2006220232, Jan. 4, 2013—39 pages.
Statutory Declaration of Mark Alexander Horsburgh in the Matter of Australian Innovation Patent No. 2011100234 in the name of Scantech International Pty Ltd. and in the Matter of an Opposition thereto by RTI Pty Ltd, Jan. 29, 2013, 2 pages.
Exhibit MAH-1—in the Matter of Australian Innovation Patent No. 2011100234 in the name of Scantech International Pty Ltd. and in the Matter of an Opposition thereto by RTI Pty Ltd, Jan. 29, 2013, 22 pages.
Exhibit MAH-2—in the Matter of Australian Innovation Patent No. 2011100234 in the name of Scantech International Pty Ltd. and in the Matter of an Opposition thereto by RTI Pty Ltd, Jan. 29, 2013, 11 pages.
Evidence in Support—part 1, Statutory Declaration of Meron Lewis for the Matter of Australian Innovation Patent No. 2011100234 in the name of Scantech International Pty Ltd. and in the Matter of an Opposition thereto by RTI Pty Ltd, Feb. 13, 2013, 80 pages.
Evidence in Support—part 2 for the Matter of Australian Innovation Patent No. 2011100234 in the name of Scantech International Pty Ltd. and in the Matter of an Opposition thereto by RTI Pty Ltd, Feb. 13, 2013, 76 pages.
Evidence in Support—part 3 for the Matter of Australian Innovation Patent No. 2011100234 in the name of Scantech International Pty Ltd. and in the Matter of an Opposition thereto by RTI Pty Ltd, Feb. 13, 2013,62 pages.
Evidence in Support—part 4 for the Matter of Australian Innovation Patent No. 2011100234 in the name of Scantech International Pty Ltd. and in the Matter of an Opposition thereto by RTI Pty Ltd, Feb. 13, 2013,46 pages.
Evidence in Answer, Statutory Declaration of Silvere Compos, in the Matter of Australian Innovation Patent No. 2011100234 in the name of Scantech International Pty Ltd. and in the Matter of an Opposition thereto by RTI Pty Ltd, Aug. 12, 2013, 10 pages.
Evidence in Answer, Statutory Declaration of Andrew Roland Harris, in the Matter of Australian Patent Application No. 2006220232 in the name of Scantech International Pty Ltd. and Opposition thereto by RTI Pty Ltd, Aug. 12, 2013, 33 pages.
Partial Evidence in Answer, Statutory Declaration of Silvere Compos, in the Matter of Australian Patent Application No. 2006220232 in the name of Scantech International Pty Ltd. and Opposition thereto by RTI Pty Ltd, Dec. 11, 2013, 22 pages.
Written Submissions—MAH 17, in the Matter of Australian Patent Application No. 2006220232 in the name of Scantech International Pty Ltd. and Opposition thereto by RTI Pty Ltd, Dec. 2013, 8 pages.
Written Submissions to Support Extension of Time Application, in the Matter of Australian Patent Application No. 2006220232 in the name of Scantech International Pty Ltd. and Opposition thereto by RTI Pty Ltd, Dec. 18, 2013, 5 pages.
Part Evidence in Answer, Statutory Declaration of Kenneth Graham Smith, in the Matter of Australian Patent Application No. 2006220232 in the name of Scantech International Pty Ltd. and Opposition thereto by RTI Pty Ltd, Jan. 3, 2014, 26 pages.
Statutory Declaration of Andrew Roland Harris, in the Matter of Australian Innovation Patent No. 2011100234 in the name of Scantech International Pty Ltd. and Opposition thereto by RTI Pty Ltd, Nov. 21, 2012, 40 pages.
Statutory Declaration of Kenneth Graham Smith, in the Matter of Australian Patent Application No. 2006220232 in the name of Scantech International Pty Ltd. and Opposition thereto by RTI Pty Ltd, Feb. 12, 2014, 8 pages.
Statutory Declaration of Dr. James Hubert Asbury, in the Matter of Australian Innovation Patent No. 2011100234 in the name of Scantech International Pty Ltd. and in the Matter of an Opposition thereto by RTI Pty Ltd, Sep. 24, 2013, 12 pages.
Statutory Declaration of Dr. James Hubert Asbury, in the Matter of Australian Innovation Patent No. 2011100234 in the name of Scantech International Pty Ltd. and in the Matter of an Opposition thereto by RTI Pty Ltd, Oct. 4, 2013, 7 pages.
Statutory Declaration of Andrew Roland Harris, in the Matter of Australian Innovation Patent No. 2011100234 in the name of Scantech International Pty Ltd. and Opposition thereto by RTI Pty Ltd, May 24, 2013, 3 pages.
Additional Evidence in Answer—Statutory Declaration of Andrew Roland Harris, in the Matter of Australian Innovation Patent No. 2011100234 in the name of Scantech International Pty Ltd. and Opposition thereto by RTI Pty Ltd, Aug. 27, 2013, 2 pages.

(56) References Cited

OTHER PUBLICATIONS

Statutory Declaration of Andrew Roland Harris, in the Matter of Australian Innovation Patent No. 2011100234 in the name of Scantech International Pty Ltd. and Opposition thereto by RTI Pty Ltd, Oct. 2, 2013, 4 pages.

* cited by examiner

ON-BELT ANALYSER SYSTEM

RELATED APPLICATIONS

This application claims priority from Australian Provisional Patent Application No. 2005900951 and U.S. Provisional Patent Application No. 60/658,195, the contents of which are incorporated herein by reference.

FIELD OF THE INVENTION

This invention relates to an on-belt analyser.

BACKGROUND OF THE INVENTION

One form of on-belt analyser, which utilises a thermal neutron capture and gamma ray production technique known as PGNAA (Prompt Gamma Neutron Activation Analysis), is employed to analyse the composition of material such as coal or other mineral product transported on a conveyor belt. The analyser has a C-shaped housing provided with lifting points to allow the analyser to be appropriately positioned across a path of the belt. The weight of the analyser is quite substantial, in the order of 6500 to 9000 kg and the lifting points are necessarily provided at a base of the analyser due to structural load-bearing limitations of the housing. Once positioned, removable side shielding is fitted to close the open side of the C-shaped housing, to thereby define a tunnel in the order of 2 meters long, through which the belt passes.

The tunnel has a radiation source in its base and sensors in the roof thereof. Tunnel slider panels are provided above the radiation source to support the belt as it passes through the analyser.

Installation and operating costs of the analyser are relatively high given the analyser generally needs to be installed in a shed or the like for protection from the elements and various component parts such as the slider panels are subject to wear during operation. Also, in order to install the analyser substantial parts of the conveyor belt support structure, such as frame work and stringer or idler wheels, need to be removed. The remaining structure, at either side of the analyser, then needs to be configured in order to ensure an appropriate profile is applied to the conveyor belt, as it enters the analyser, compatible with the shape of the tunnel and the slider panels.

OBJECT OF THE INVENTION

The present invention seeks to provide an improved analyser system.

SUMMARY OF THE INVENTION

In accordance with the invention, there is provided an analyser system including an on-belt analyser having a housing adapted to be positioned across a path of a conveyor belt which carries material to be analysed, wherein the housing defines a tunnel dimensioned to allow the belt to travel therethrough in suspended relation in order to allow analysis of the material without the belt contacting the analyser.

In another aspect there is provided an on-belt analyser with a C-shaped housing, to allow the analyser to be positioned across a path of a conveyer belt, wherein an upper arm of the housing includes lifting points.

In another aspect, there is provided an analyser with a housing adapted to be positioned across a path of a conveyor belt and a canopy for protecting the housing.

Preferably, the canopy is fitted to lifting points located on an upper arm of the housing.

Preferably, the housing defines a tunnel through which the conveyor belt passes and has extension panels fitted thereto to provide protection adjacent the analyser and external of the tunnel, from radiation emissions generated from a radiation source within the analyser.

In another aspect, there is provided an analyser including a housing adapted to be positioned across a path of a conveyor belt, wherein the housing defines a tunnel arranged to receive the belt such that the belt passes through the tunnel without contacting the analyser.

In another aspect, there is provided an analyser system including an analyser with a housing, which defines a tunnel, and a conveyor assembly with a conveyor belt that passes through the tunnel without contacting the analyser.

Preferably, the housing has a width dimension in the order of 1 meter to allow the analyser to be positioned between existing adjacent supporting idlers of the conveyor belt.

Preferably, an under side of the belt has a clearance in the order of 30 mm from a base of the tunnel.

Preferably, the weight of the analyser is in the order of 2000 kg.

BRIEF DESCRIPTION OF THE DRAWINGS

The invention is described by way of non-limiting example only, with references to the accompanying drawings, in which.

DETAILED DESCRIPTION

Figure 1:
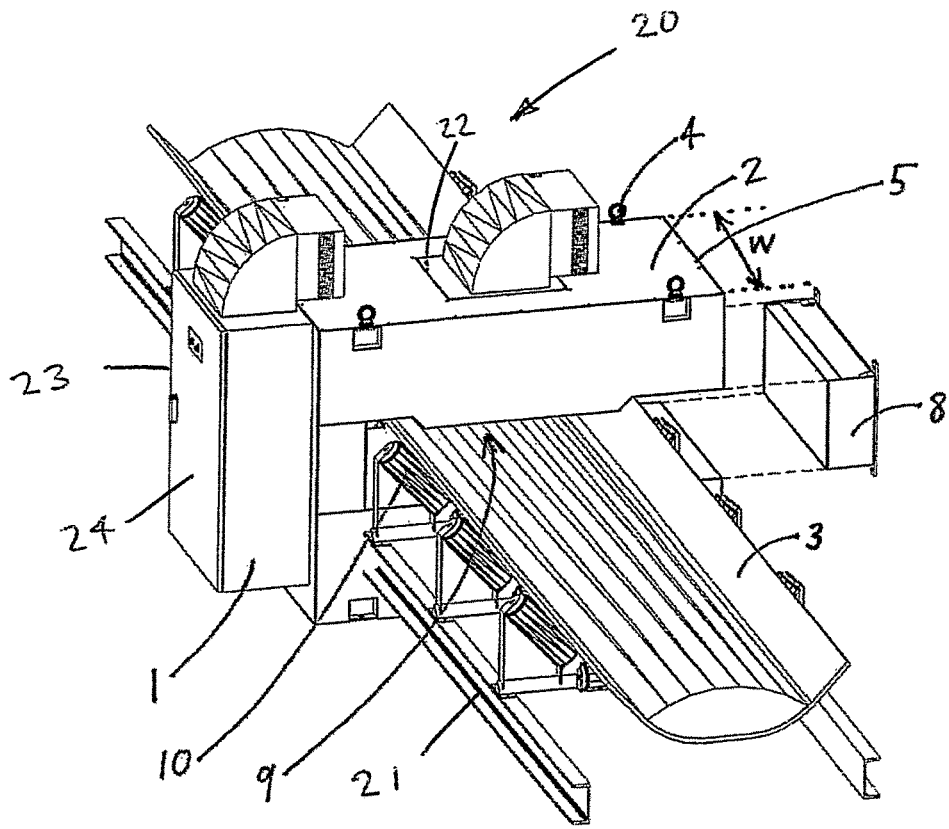
FIG. 1 is a perspective view of an analyser.

An analyser system 20 is shown in FIG. 1 as including an analyser 1 and a conveyor assembly 21. The analyser 1 has a C-shaped housing 2 arranged to be positioned across a path of a conveyor belt 3 of the assembly 21. The analyser 1 is designed so as to weigh only in the order of 2000 kg which is light enough for the housing 2 to maintain structural integrity even if lifted from lifting points 4 provided by eye-bolts, which are provided on an upper arm 5 of the analyser 1. For that purpose, the analyser 1 is preferably formed of a steel framed enclosure filled with cast neutron shielding (CNS). The CNS is a dense suspension of 60% high-density polyethylene beads cemented together with a mixture of 20% borax and 20% polyester resin-plus catalyst. This material provides most of the shielding required since it is effective in slowing down and absorbing neutrons. The material is also waterproof, non-corrosive and intrinsically fire resistant.

Once the analyser 1 is positioned in the manner shown, side shield 8 is fastened in place so that the analyser defines a tunnel 9 through which the belt 3 passes. A width dimension "w" of the analyser is preferably in the order of 1 meter to allow the analyser to be positioned between existing supporting structure, such as idlers 10, of the conveyor assembly 21, which are conventionally spaced at between 1.2 and 1.5 meters apart.

Figure 2:
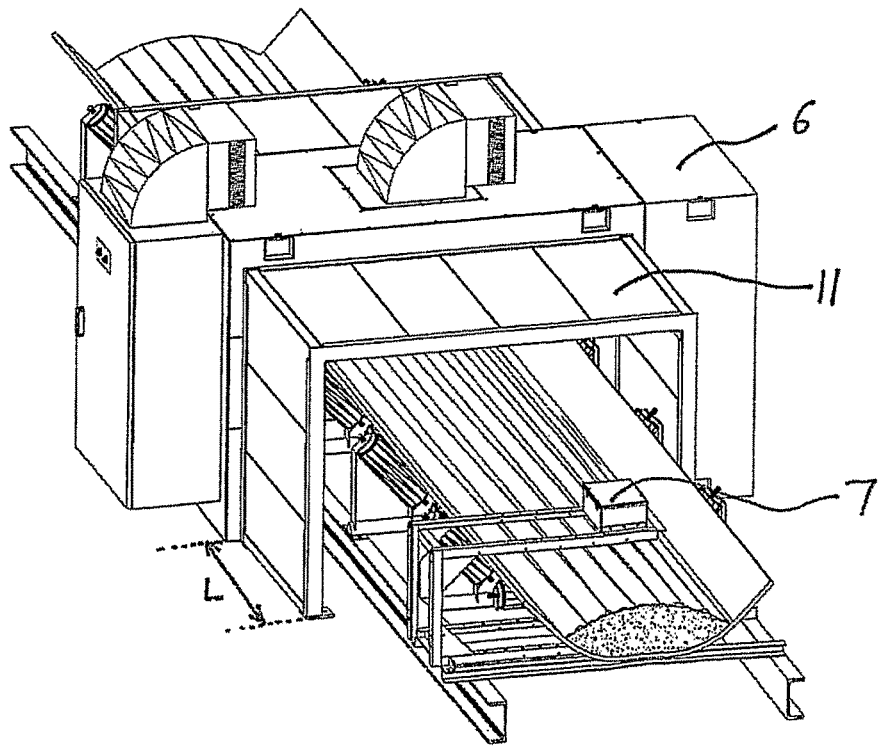
FIG. 2 is a perspective view of the analyser of FIG. 1, fitted with extension panels, automatic source drive shield, and canopy.

In some circumstances, it may be necessary to provide additional shielding for radiation protection and, in that case, a further side shield 6 may be provided and extension panels 11 may be fitted either side of the tunnel, as shown in FIG. 2. The extension panels are preferably formed of LTV stabilised polyethylene or like material, which is suitable for absorbing radiation from, for example, a Cf-252 source. The panels 11 may be dimensioned so as to provide protection for an additional length "L" of, say, 1 meter either side of the analyser 1.

FIG. 2 also shows the system 20 as including an optional microwave moisture content analyser 7 positioned above the belt 3.

Figure 3:
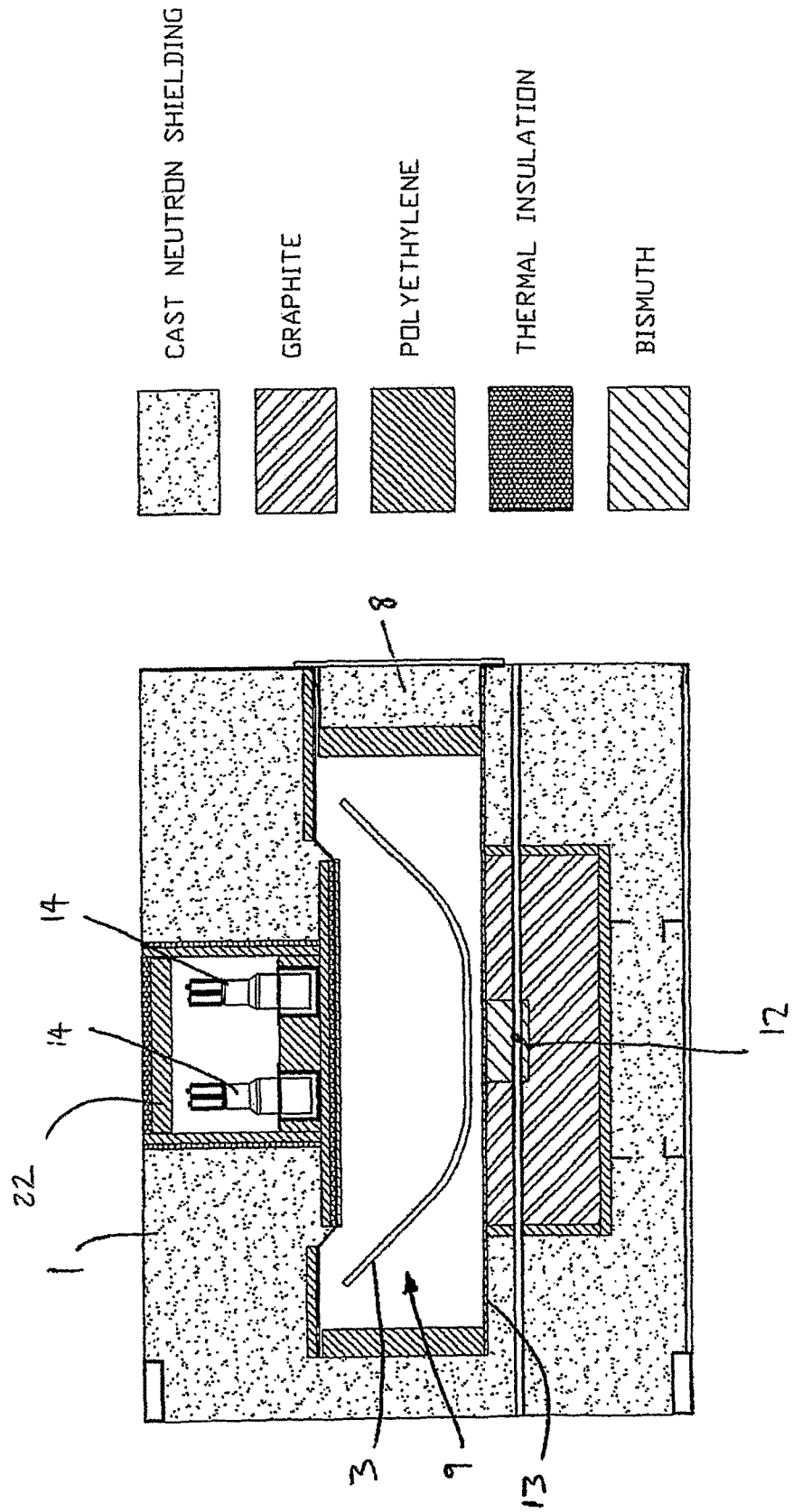
FIG. 3 is a cross-sectional view of the analyser.
Figure 5A:
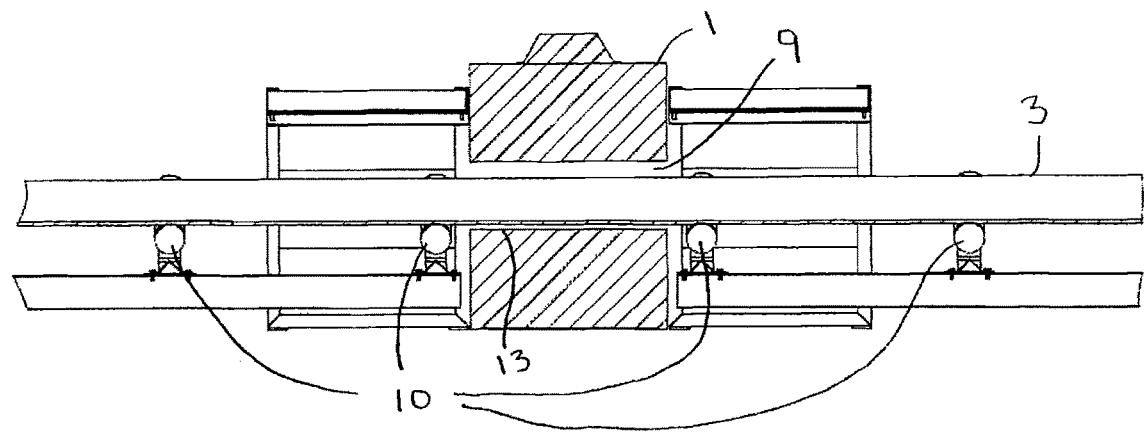
FIG. 5A is another cross-sectional view of the analyser from a view point that is perpendicular to FIG. 3.
Figure 5B:
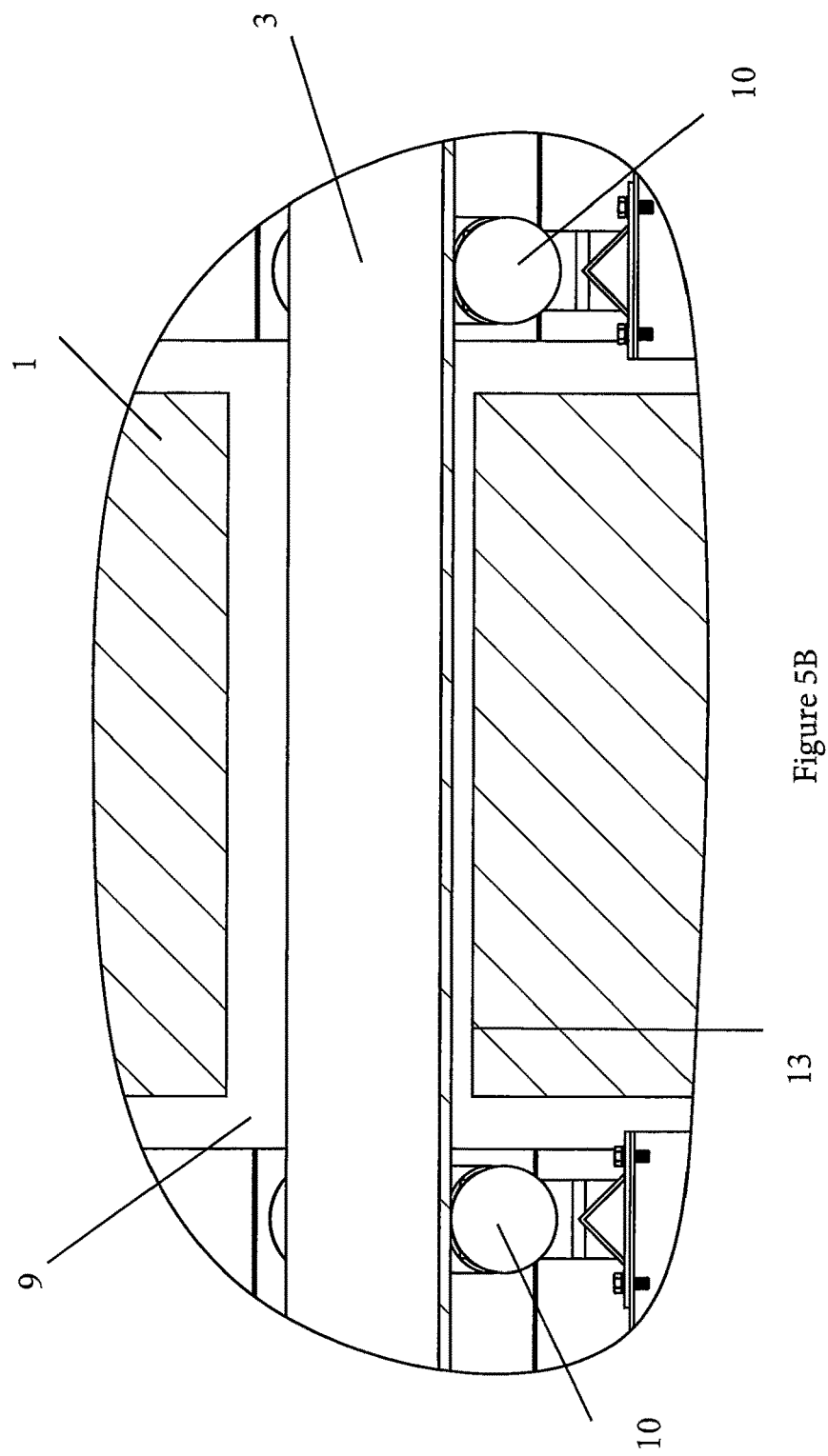
FIG. 5B is an enlarged view of the center area of the analyser in FIG. 5A.

Referring now to FIG. 3, a cross-section of the analyser 1 is shown in detail with the side shielding 8 attached to the housing 2, so as to define the tunnel 9. A radiation source 12 is provided in a base 13 of the tunnel and detectors 14 are appropriately located above the tunnel 9. The tunnel 9 is positioned and dimensioned so as to receive the conveyor belt 3 in an elevated position relative to the base 13 of the tunnel 9. The clearance is preferably in the order of 30 mm to allow for a slight droop in the belt 3 between its supporting idlers 10. Previously, it was considered critical to minimise the distance between the Cf-252 source and material to be analysed in order to maximise absorption of neutrons in the material. Accordingly, the prior-art analyser was designed to have contact between the belt and the analyser using 25 mm thick slider panels. The geometry of the analyser illustrated in FIG. 3, however, has been investigated using a program called MCNP (Monte Carlo N-particle) and it has been found that replacing the slider panels with air made little difference. Accordingly, a clearance is provided between the belt 3 and the base 13 of the tunnel 9, which allows the previous slider panels to be dispensed with, thereby reducing construction and maintenance costs. The tunnel 9 is shaped to accommodate conveyor belts 3 from 600 mm to 1400 mm wide with trough angles from 30° to 45° with no modification to belt 3 or tunnel 9. As a result of the relative clearance, an additional advantage is realised in that belt clips and staples (not shown) cannot damage analyser 1. Another cross-section of the analyser 1 is shown in FIG. 5, wherein the belt 3 is elevated above the base 13 of the tunnel 9 such that the belt 3 traveling through the tunnel 9 is without being supported within the tunnel 9. The belt 3 is supported by its supporting idlers 10 provided outside the tunnel 9. This can be seen in more detail in FIG. 5B.

Figure 4:
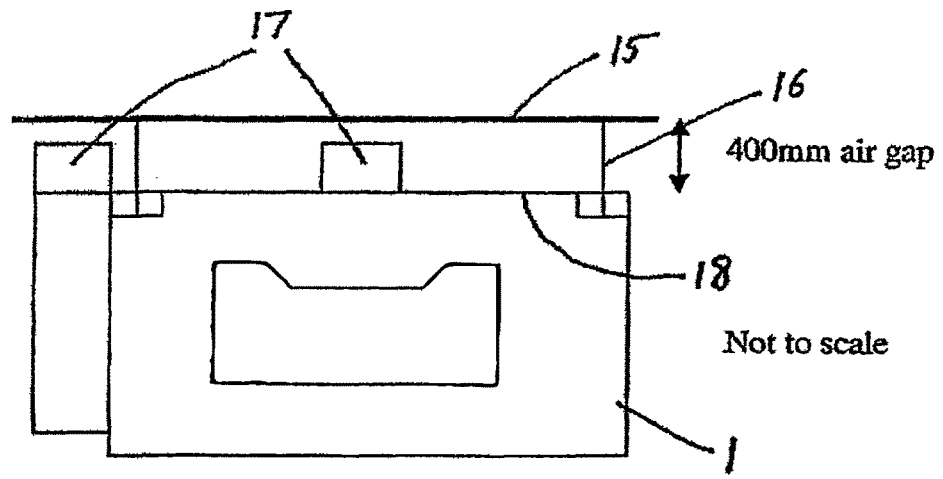
FIG. 4 is a diagrammatic end view of the analyser with a canopy.

Turning now to FIG. 4, the analyser 1 is shown with a canopy 15 supported on struts 16 fixed to the lifting points 4. The canopy 15 is preferably formed of 3 mm thick steel or fibreglass and stands approximately 400 mm above the analyser 1, leaving an approximate clearing of 50 mm above the 350 mm high air conditioners 17. The canopy 15 provides protection to the top 18 of the analyser 1 from direct sunlight, rain and snow. The canopy 15 should also minimise dust build-up on and around the air conditioner 17. Provision of the canopy 15 additionally allows the analyser to be installed in an external environment at any desired location along the length of the conveyor belt 3, as compared to the prior art analyser, which needed to be installed within a shed. As such, the analyser 1 provides for further reduction in installation costs.

In addition to the above, the prior-art analyser used proprietary analogue electronics and NaI (sodium iodide crystal) detectors. The present analyser 1, on the other hand, uses off-the-shelf digital multi-channel analysers and bismuth germinate crystal (BGO) detectors.

The digital multi-channel analysers provide more consistent, linear, stable spectra and are more reliable as compared to the previous analyser electronics, for which components are becoming obsolete. The BGO detectors capture more gamma rays and have better photo-peak fraction due to higher crystal density, have better peak to background ratio (ie better signal-to-noise ratio) and better linearity. The detectors 14 and associated multi-channel analyser electronics are preferably located within a single common air-conditioned, temperature-controlled detector enclosure 22 to simplify operational and construction requirements. The remaining electronics such as an analyser computer and other electronics modules are likewise located within a single air-conditioned, temperature-controlled electronics cabinet 23, which has a sealed and locked door 24.

As such, the above-described analyser 1 provides a number of advantages over the prior-art analyser, which result from internal componentry, reduced weight and dimensions, as well as the provision of a canopy and the clearance between the analyser and a conveyor belt passing through the analyser tunnel. As may be appreciated then, the analyser may be installed on an existing conveyor assembly with minimal modification or removal of steel work of the belt support structure since the analyser is of a width sufficient to fit between pre-existing idlers and does not contact the belt so the supporting structure does not need to be configured in any particular fashion necessary to form a specific belt profile suitable for the tunnel, as compared to the prior-art analyser arrangement.

Further and more particular details of a preferred form of analyser are provided in Applicant's publications "On Belt Analyser Operation & Maintenance Manual" Version 1.3, September 2005; "On Belt Analyser-5 Health & Safety Review" Version 1.6, February 2006; and "On Belt Analyser Installation Manual" Version 7.3, October 2005, the contents of which are incorporated herein by reference.

The invention has been described, by way of non-limiting example only, and many modifications and variations may be made thereto, without departing from the spirit and scope of the invention, as described.

The invention claimed is:

1. A bulk material analyser configured to analyse an elemental composition of bulk material in the form of coal, minerals, cement raw materials, or the like, comprising:
   a housing defining an enclosed tunnel for receiving a conveyor belt carrying the bulk material to be analysed;
   a neutron source configured to emit neutrons into the material in the tunnel for interaction with the material disposed therein; and
   a gamma ray detector to detect gamma rays emitted from the material in response to the neutron interaction,
   wherein the conveyor belt is unsupported by the analyser within the enclosed tunnel.

2. The bulk material analyser according to claim 1, wherein the conveyor belt travels through the tunnel in a freely suspended state so that the conveyor belt is not subject to wear within the enclosed tunnel.

3. The bulk material analyser according to claim 2, wherein the width of the analyser, in a direction lengthwise of the conveyor belt, is in the order of 1 meter.

4. The bulk material analyser according to claim 2, arranged whereby a clearance in the order of 30 mm is provided between the conveyor belt and a base of the enclosed tunnel.

5. The bulk material analyser according to claim 2, wherein extension panels are fitted on either side of the enclosed tunnel to provide protection adjacent the analyser and external of the enclosed tunnel, from radiation emissions generated by the neutron source within the analyser.

6. The bulk material analyser according to claim 1, wherein the housing is adapted to be positioned across a path of an existing conveyor belt without disrupting the existing conveyor belt.

7. The bulk material analyser according to claim 6, wherein the housing comprises a C-shaped portion which allows the housing to be retro-fitted across a bulk material conveyor belt, and a removable side portion, the C-shaped portion and the side portion together defining the enclosed tunnel through which the conveyor belt passes.

8. The bulk material analyser according to claim 1, wherein the enclosed tunnel is configured to receive a conveyor belt of between 600 mm and 1400 mm in width, with a trough angle of between 30° and 45° without requiring any modification to the conveyor belt profile.

9. The bulk material analyser according to claim 1, further comprising a conveyor assembly with idlers arranged to support the conveyor belt at either side of the enclosed tunnel so as to suspend the conveyor belt in an elevated position relative to the base of the enclosed tunnel as the conveyor belt passes through the enclosed tunnel.

10. The bulk material analyser system according to claim 9, wherein the idlers are spaced at between 1.2 and 1.5 meters apart.

11. The bulk material analyser according to claim 1, further comprising lifting points at an upper section of the housing.

12. The bulk material analyser according to claim 1, further comprising a canopy for protecting the analyser.

13. The bulk material analyser according to claim 1, wherein the neutron source and detector are configured for analysis using Prompt Gamma Neutron Activation Analysis (PGNAA).

14. The bulk material analyser according to claim 1, further comprising multi-channel analyser electronics, wherein the gamma ray detector and the multi-channel analyser electronics are located within a common air conditioned, temperature-controlled detector enclosure.

15. The bulk material analyser according to claim 1, wherein the neutron source is disposed below the conveyor belt, and the gamma ray detector is disposed above the conveyor belt.

16. A bulk material analyser configured to analyse an elemental composition of bulk material in the form of coal, minerals, cement raw materials, or the like, comprising:
   a housing defining an enclosed tunnel for receiving a conveyor belt carrying a bulk material to be analysed;
   a neutron source to emit neutrons into an interaction region within the enclosed tunnel for interaction with the bulk material disposed therein; and
   a gamma ray detector to detect gamma rays emitted from the material in response to the neutron interaction,
   wherein a conveyor belt carrying the material is unsupported in the enclosed tunnel so as not to be subject to wear in the enclosed tunnel.

17. The bulk material analyser according to claim 16, wherein the gamma ray detector is disposed above the interaction region, and the neutron source is disposed below the interaction region.

18. A bulk material analyser configured to analyse an elemental composition of bulk material in the form of coal, minerals, cement raw materials, or the like, comprising:
   a neutron source;
   a gamma ray detector; and
   a housing adapted to be positioned across a path of a conveyor belt which carries material to be analysed,
   wherein the housing defines an enclosed tunnel dimensioned to allow the conveyor belt to pass above the neutron source, below the gamma ray detector, and through the tunnel without being supported within the enclosed tunnel.

19. A bulk material analyser configured to analyse an elemental composition of bulk material in the form of coal, minerals, cement raw materials, or the like, comprising:
   a neutron source;
   a detector; and
   a housing adapted to be positioned across a path of a conveyor belt which carries bulk material to be analysed,
   wherein the housing defines an enclosed tunnel dimensioned to allow the conveyor belt to pass above the neutron source, below the gamma ray detector, and through the enclosed tunnel without being supported within the enclosed tunnel so that the portion of the conveyor belt within the enclosed tunnel can be suspended between support idlers external to the enclosed tunnel.

* * * * *